(12) United States Patent
Song et al.

(10) Patent No.: US 10,525,105 B2
(45) Date of Patent: Jan. 7, 2020

(54) PEPTIDE FOR REPAIRING CARTILAGE AND TREATING OSTEOARTHRITIS

(71) Applicant: Guangzhou Link Health Pharma Co., Ltd., Guangzhou (CN)

(72) Inventors: Yan Song, Guangzhou (CN); Yuansheng Xu, Guangzhou (CN); Xiaoyu Lu, Guangzhou (CN)

(73) Assignee: GUANGZHOU LINK HEALTH PHARMA CO., LTD., Guangzhou (CN)

( * ) Notice: Subject to any disclaimer, the term of this patent is extended or adjusted under 35 U.S.C. 154(b) by 0 days.

(21) Appl. No.: 16/470,976

(22) PCT Filed: Dec. 12, 2017

(86) PCT No.: PCT/CN2017/115532
§ 371 (c)(1),
(2) Date: Jun. 19, 2019

(87) PCT Pub. No.: WO2018/121235
PCT Pub. Date: Jul. 5, 2018

(65) Prior Publication Data
US 2019/0314453 A1 Oct. 17, 2019

(30) Foreign Application Priority Data

Dec. 29, 2016 (CN) .......................... 2016 1 1243856

(51) Int. Cl.
*A61K 38/18* (2006.01)
*A61K 9/00* (2006.01)
*A61P 19/04* (2006.01)

(52) U.S. Cl.
CPC ........ *A61K 38/1875* (2013.01); *A61K 9/0019* (2013.01); *A61P 19/04* (2018.01)

(58) Field of Classification Search
None
See application file for complete search history.

(56) References Cited

U.S. PATENT DOCUMENTS

2014/0079753 A1* 3/2014 Darby .................. C07K 14/685
424/423

FOREIGN PATENT DOCUMENTS

| CN | 1382803 A | 12/2002 |
| CN | 1752103 A | 3/2006 |
| CN | 1951964 A | 4/2007 |
| CN | 103079585 A | 5/2013 |
| CN | 106749606 A | 5/2017 |

OTHER PUBLICATIONS

Li, Jinfeng et al. Repair of Rabbit Radial Bone Defects Using True Bone Ceramics Combined With BMP-2-Related Peptide and Type I Collagen. Materials Science and Engineering C. Oct. 12, 2010, 30(8), pp. 1272-1279.

Kazuhiro Aoki et al., Peptide-based Delivery to Bone, Advanced Drug Delivery Reviews, Sep. 2012, vol. 64, pp. 1220-1238.

* cited by examiner

*Primary Examiner* — Fred H Reynolds
(74) *Attorney, Agent, or Firm* — Gokalp Bayramoglu (57) ABSTRACT

A BM23 peptide is obtained by mutating and modifying BMP-2. The BM23 peptide improves stability and duration of in-vivo efficacy relative to BMP-2, has an activity of promoting the differentiation of bone marrow mesenchymal stem cells into chondrocytes and promoting the proliferation of chondrocytes and can be used for repairing cartilage and/or treating osteoarthritis.

19 Claims, 8 Drawing Sheets
Specification includes a Sequence Listing.

PEPTIDE FOR REPAIRING CARTILAGE AND TREATING OSTEOARTHRITIS

CROSS REFERENCE TO THE RELATED APPLICATIONS

This application is the national phase entry of International Application No. PCT/CN2017/115532, filed on Dec. 12, 2017, which is based upon and claims priority to Chinese Patent Application No. 201611243856.7, filed on Dec. 29, 2016, the entire contents of which are incorporated herein by reference.

TECHNICAL FIELD

The present invention generally relates to the field of peptides, and more particularly to a peptide for repairing cartilage and/or treating osteoarthritis and a medicament containing the peptide.

BACKGROUND

Osteoarthritis (OA) is a common joint disease, characterized by joint pain and stiffness; and cartilage damage is the main cause of osteoarthritis. Osteoarthritis occurs more frequently in people after middle age, and more frequently in female than in male. The prevalence of osteoarthritis is 10%-17% in 40-year-olds, 50% in people aged 60 and above, and as high as 80% in people aged 75 and above. Osteoarthritis has a certain disability rate. With the aging of the population, osteoarthritis will become an important issue affecting quality of people's life, and the market demand for osteoarthritis drugs will continue to expand.

Currently, the therapeutic drugs for osteoarthritis in clinical practice are classified into specific therapeutic drugs and non-specific therapeutic drugs. The non-specific therapeutic drugs, such as non-steroidal anti-inflammatory drugs, are mainly used for analgesia and symptom control, but have no protective effect on cartilage. The specific therapeutic drugs, such as glucosamine, chondroitin sulfate, diphosphonate, etc., can protect articular cartilage and delay the progression of osteoarthritis. However, the specific therapeutic drugs generally have a relatively slow-acting effect, requiring several weeks of treatment. Moreover, the specific therapeutic drugs have no effect on the regeneration of damaged cartilage. Therefore, developing a novel osteoarthritis drugs with good safety and outstanding efficacy has become a major goal in the medical field.

Cartilage damage is a main cause of osteoarthritis. Articular cartilage is composed of abundant extracellular matrix (ECM) and a limited number of chondrocytes embedded in the EMC. The metabolism of chondrocytes is regulated by many cytokines, among which, bone morphogenetic protein (BMP) plays an important role in the synthesis and metabolism of bone and cartilage.

Bone morphogenetic protein, also known as bone formation protein, is an acidic polypeptide capable of inducing bone formation and chondrogenesis at an ectopic site outside of bone. BMP is a hydrophobic acid glycoprotein with a molecular weight of 18000 D and is composed of more than ten kinds of amino acids. BMP has stable performance under acidic conditions and has a certain solubility in a solution with a pH of 7.2. When the pH of the solution is greater than 8.5, BMP is completely inactivated.

BMPs are a group of multifunctional growth factors belonging to the TGF-β superfamily, and more than 20 family members have been identified and described. A large number of literatures indicate that BMP can induce mesenchymal cells to proliferate and differentiate into osteoblasts or chondrocytes. BMP plays a key role in the occurrence, induction and repair of bone, and can affect growth, differentiation and apoptosis of cells. BMP can significantly promote the growth and maturation of cultured chondrocytes, and plays a key role in the occurrence and development of various tissues.

BMP-2 is an acidic polypeptide, and has a strongest ability of inducing bone marrow mesenchymal stem cells to differentiate into osteoblasts among the BMP superfamily. However, the half-life of the BMP-2 is relatively short, the therapeutic concentration of BMP-2 is difficult to maintain, and BMP-2 cannot act on more target cells in an effective time, so the induction activity of BMP-2 cannot be fully exerted, and the clinical application of BMP-2 has been greatly limited. Currently, recombinant BMP-2 is the most commonly studied BMP-2 drugs. As mentioned above, BMP-2 has poor stability and short half-life, so there is an urgent need to develop a novel drug to overcome the defects of recombinant BMP-2.

SUMMARY

The present invention aims to develop a stable novel peptide which can be used for repairing cartilage and/or treating osteoarthritis by using the amino acid sequence of BMP-2 as a source.

The objective of the present invention is achieved by the following technical solutions:

In a first aspect, the present invention relates to a peptide (referred to as BM23 peptide) for repairing cartilage and/or treating osteoarthritis. The peptide is obtained by mutating and modifying the polypeptide fragment of natural BMP-2. The peptide contains 23 amino acids, having the amino acid sequence of:

GlnLeuLysHisArgAsnHarHisArgIleLysThrGlySerThrAsn-HisGlyLeuValGlnSerLeu (SEQ ID NO: 1), wherein the $1^{st}$ amino acid is D-glutamine, the $7^{th}$ amino acid is homoarginine, and the $23^{rd}$ amino acid is amidated leucine.

Preferably, the peptide can be used to repair cartilage, and/or to treat osteoarthritis.

Preferably, the carboxyl terminus of the peptide may be subjected to a modification, including amidation or carbonylation, preferably subjected to the amidation.

Preferably, an effective dose of the peptide for a treatment of cartilage damage and/or osteoarthritis is 1-10 mg.

Preferably, the peptide can be modified to form a chimeric molecule, and the chimeric molecule includes a fusion protein formed by a fusion of the peptide with an immunoglobulin constant region (Fc) or human serum albumin (HSA).

Preferably, the peptide is used to treat osteoarthritis in combination with other osteoarthritis drugs, including hyaluronic acid, non-steroidal anti-inflammatory drugs, etc.

In a second aspect, the present invention relates to a pharmaceutically acceptable salt of the BM23 peptide, including acetates, hydrochlorides, phosphates or acetates, preferably to the acetates.

In a third aspect, the present invention relates to a drug, characterized in that, the drug contains the BM23 peptide at a therapeutically effective dose and a pharmaceutically acceptable carrier.

Preferably, the pharmaceutically acceptable carrier is a saline solution, and the drug is injectable.

Preferably, the pharmaceutically acceptable carrier is a colloidal solution, including a hyaluronic acid gel, and the drug is injectable.

Preferably, the drug is administered by injection, including a knee articular cavity injection or a subcutaneous injection.

In a fourth aspect, the present invention relates to applications of the BM23 peptide in the preparation of drugs for repairing cartilage and/or for treating osteoarthritis.

Compared with the prior art, the present invention has the following advantages: the BM23 peptide of the present invention overcomes the disadvantages of unstable and short half-life of BMP-2 drugs, has significantly improved stability and in-vivo efficacy duration, and has the activity of promoting the differentiation of mesenchymal stem cells into chondrocytes and promoting the proliferation of chondrocytes, thereby facilitating the repair of damaged cartilage, and relieving the symptoms of osteoarthritis.

DETAILED DESCRIPTION OF THE EMBODIMENTS

The present invention will be described in detail below along with specific embodiments. The following embodiments are intended to facilitate the further understanding of the present invention by those skilled in the art, but are not intended to limit the invention in any way. It should be noted that many modifications and improvements without departing from the inventive concept of the present invention may be made by those skilled in the art. Those modifications and improvements shall be considered as falling within the protective scope of the present invention.

Embodiment 1

Solid-Phase Synthesis of BM23 Peptide

Figure 1:
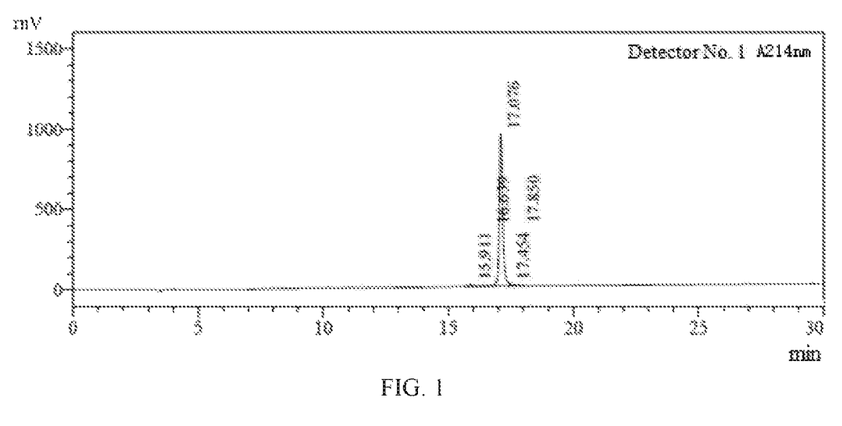
FIG. 1 shows a high performance liquid chromatography (HPLC) detection of a BM23 peptide obtained by a solid-phase synthesis method.

BM23 peptide (SEQ ID NO: 1, in which the $1^{st}$, $7^{th}$ and $23^{rd}$ amino acids are D-glutamine, homoarginine and amidated leucine, respectively) was entrusted to ABbiochem Co., Ltd. for synthesis by using a conventional solid-phase process, and a purity of a synthesized peptide is larger than 98%, as shown in FIG. 1.

Embodiment 2

Isolation and Culture of Mesenchymal Stem Cells (BMSCs)

Three SD rats aged 8 weeks were sacrificed by a dislocation method and disinfected with 70% ethanol for 5 minutes. The abdominal wall layers of the three SD rats were then cut with scissors, an incision of each SD rat was pulled to a femur, and muscles on the femur were carefully separated.

A middle of the femur was cut off, and a bone marrow cavity was repeatedly washed by a low-sugar DMEM medium (containing 1 mL/L of heparin) sucked with a syringe to flush out bone marrow.

The bone marrow was repeatedly washed with the syringe, and prepared into a single cell suspension by successively passing through needle No. 7 and needle No. 4.

The single cell suspension was centrifuged (1500 r/min, 10 min), and a supernatant was discarded; DMEM-F12 complete medium containing 10% FBS was added, and then an inoculation was performed in a culture flask at a density of $10^7$ cells/mL, and the culture flask was placed in an incubator having 5% $CO_2$ at 37° C. for a culture.

The cells were purified by a differential adherent culture. The culture solution was changed 48 hours after the inoculation, and thereafter, the culture solution was changed every 3 days to remove non-adherent hematopoietic cells.

After the cells grew to 80%-90%, a passage was performed. The culture solution was removed, and the cells were washed with PBS to remove residual serum; and the PBS was removed.

A BMSCs digestive juice (containing 0.25% trypsin and 0.02% EDTA solution) was added for a slight shaking until the BMSCs digestive juice just covers the bottom of the culture flask; and a digestion time was about 5 minutes. Then, the passage was carried out.

Figure 2A:
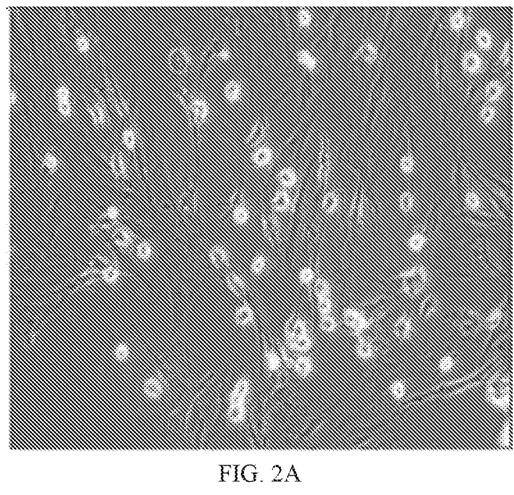
FIG. 2A is a photomicrograph showing isolated cultured rat bone marrow mesenchymal stem cells (BMSCs) after a primary isolated P0 culture of rat BMSCs (10×10 magnification).
Figure 2B:
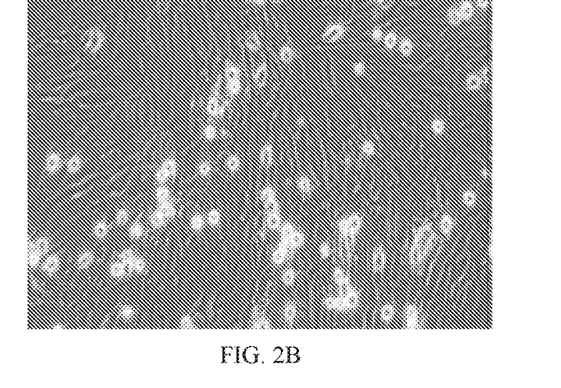
FIG. 2B is a photomicrograph showing isolated cultured rat bone marrow mesenchymal stem cells (BMSCs) after a first passage P1 culture after a primary isolation of rat BMSCs (10×10 magnification).

The cells were transferred to a centrifuge tube, centrifuged at 1500 r/min for 10 minutes; a supernatant was removed; and a complete culture medium of mesenchymal stem cells was added for re-suspending the cells. The results are as shown in FIGS. 2A and 2B.

Embodiment 3

Effect of BM23 Peptide on Differentiation of Mesenchymal Stem Cells In Vitro

Chondrogenic Induction

The BM23 peptide was dissolved in phosphate buffered saline (PBS).

The cells were re-suspended in a complete chondrogenic medium (purchased from Guangzhou Cyagen Biosicences Inc., Item No.: RASMX-90011) containing different concentrations of BM23 peptides (0.1 μM, 0.3 μM, and 1 μM), so that the concentration of BMSCs was $5.0 \times 10^5$ cells per ml. PBS was used as a negative control, and 1 μM human insulin growth factor (IGF-1, purchased from Beijing Yiqiao Shenzhou Biotechnology Co., Ltd.) was used as a positive control.

The treated BMSCs were incubated at 37° C. under 5% $CO_2$ saturated humidity. The medium was changed every 2-3 days, and 0.5 mL of fresh complete chondrogenic medium was added to each tube.

Generally, samples can be collected after 28 days of continuous induction; and cartilage balls can be subjected to formalin fixation, paraffin embedding, sectioning and alcian blue staining.

Quantitative PCR Detection

Total RNA extraction: cells were collected, total RNA was extracted by a Trizol method, and cDNA was obtained by a reverse transcription. The reaction conditions were: incubation at 30° C. for 10 minutes; incubation at 42° C. for 60 minutes; and incubation at 85° C. for 10 minutes.

PCR:

Quantitative PCR was performed using cDNA as a template and the following primers:

(1) rat COL2A1-F1: 5' GCGGAGACTACTGGATTGAT 3' (as shown in SEQ ID NO: 2)
(2) rat COL2A1-R1: 5' CGTTCATGGTCTCTCCAAAC 3' (as shown in SEQ ID NO: 3)
(3) rat ACAN-F1: 5' GAGTTCCCAGATCTGCATGG 3' (as shown in SEQ ID NO: 4)
(4) rat ACAN-R1: 5' TGGTGCTGACGGTAACATTC 3' (as shown in SEQ ID NO: 5)

Reaction conditions: 50° C. for 2 minutes; 95° C. for 2 minutes; 95° C. for 15 seconds, 60° C. for 32 seconds, 40 cycles.

Melting curve analysis: temperature 60° C.-95° C. The analysis was repeated 3 times for each sample.

Paraffin Embedding of Tissues:

The specimens were fixed with 4% paraformaldehyde for 24-36 hours.

The specimens were taken out and washed to remove the fixative, and a material with a suitable size (about 0.2 cm in thickness) was cut for embedding.

The specimens were respectively treated once with 70%, 80%, 90% and 95% ethanol, and 60 minutes are for each treatment. The specimens were treated twice with 100% ethanol, and 50 minutes are for each time.

The specimens were treated once with ½xylene-½ absolute ethanol for 15 minutes. The specimens were treated twice with xylene, and 15 minutes are for each time. The specimens were placed in Paraffin wax (60° C.) twice, and 60 minutes are for each time. Finally, the paraffin embedding was performed.

Immunohistochemical Detection:

Paraffin-embedded tissue slices were dewaxed twice with xylene, and 10 minutes are for each time. The paraffin-embedded tissue slices were respectively treated once with 100%, 95%, 85%, 75%, 50% ethanol and pure water, successively, and 5 minutes are for each treatment.

The slices were washed with PBS for 5 minutes, and incubated in a wet box with hydrogen peroxide at room temperature for 10 minutes, and then washed with PBS for 3 times, and 5 minutes for each time.

The slices were placed in a microwave oven, and heated on high heat to boil, and kept on low heat to boil for 8 minutes (the slices were immersed in citric acid antigen repair solution), and when the temperature of the solution was naturally decreased to room temperature, the slices were washed with PBS for 5 minutes.

The slices were sealed with 10% normal goat serum in a wet box at room temperature for 30 minutes, incubated with a primary antibody at 4° C. overnight, and washed with PBS for 3 times, and 5 minutes are for each time; the slices were incubated with a secondary antibody in the wet box at room temperature for 30 minutes, and washed with PBS for 3 times, and 5 minutes are for each time. The slices were treated with DAB (3,3'-diaminobenzidine) for coloration, and washed with PBS for 3 times, and 5 minutes are for each time. A hematoxylin redyeing was performed; and the slices were washed with water to remove excess dye, differentiated for a few seconds, washed with water until turned back to blue. The slices were subjected to gradient dehydration once respectively with 50%, 75%, 85%, 95% and 100% ethanol, treated with xylenes twice for transparency, and 5 minutes are for each time, and neutral gum mounting was performed.

Results

1. Induction Effect of BM23 Peptide on the Gene Expression of COL2A1 and ACAN

Figure 3:
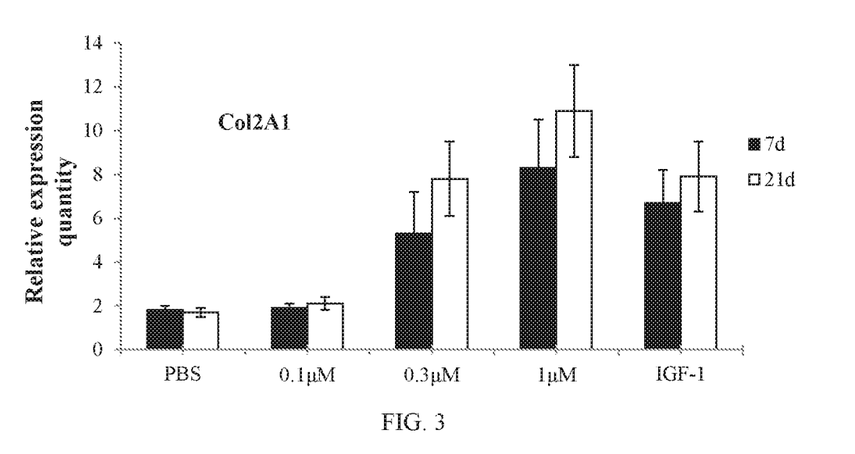
FIG. 3 shows an effect of a BM23 peptide on an expression of type II collagen (COL2A1) mRNA; a relative expression quantity of COL2A1 mRNA was detected by a quantitative PCR, PBS was used as a negative control, and human insulin growth factor (IGF-1) was used as a positive control.
Figure 4:
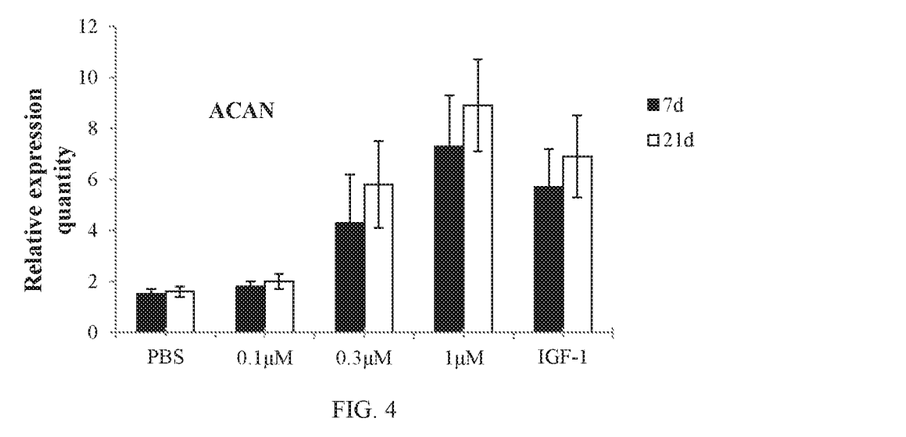
FIG. 4 shows an effect of a BM23 peptide on an expression of aggrecan (ACAN) mRNA; a relative expression quantity of ACAN mRNA was detected by a quantitative PCR, PBS was used as a negative control, and IGF-1 was a positive control.

The mRNA expression levels of COL2A1 and ACAN induced by different concentrations of BM23 peptide changed, and showed obvious dose-effect relationship and time-effect relationship. Specifically, the mRNA expression levels of COL2A1 and ACAN increased with the increase of the concentration of BM23 peptide; compared with PBS treatment, 0.1 μM BM23 peptide treatment had no significant effect; and the treatment effects of 0.3 μM and 1 μM BM23 peptides were significantly different. Moreover, the promotion effect of BM23 peptide on the mRNA expression levels of COL2A1 and ACAN were increased with time, and the expression level at the $21^{st}$ day was higher than that at the $7^{th}$ day. The results are as shown in FIGS. 3 and 4.

2. Immunohistochemical Results of COL2A1

Figure 5A:
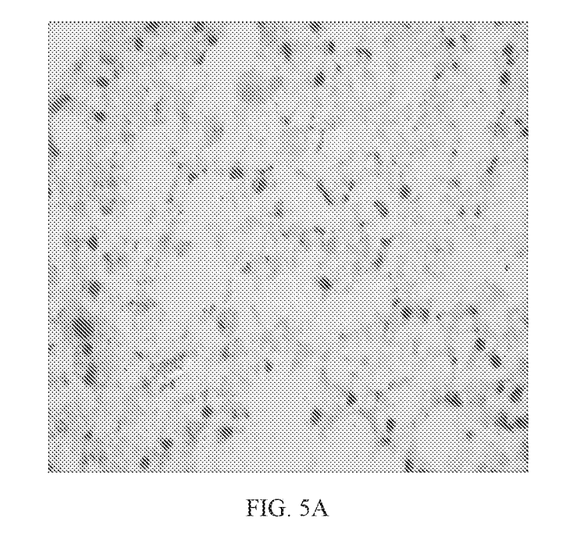
FIG. 5A shows an immunohistochemical result for COL2A1 in mesenchymal stem cells treated with a PBS.
Figure 5B:
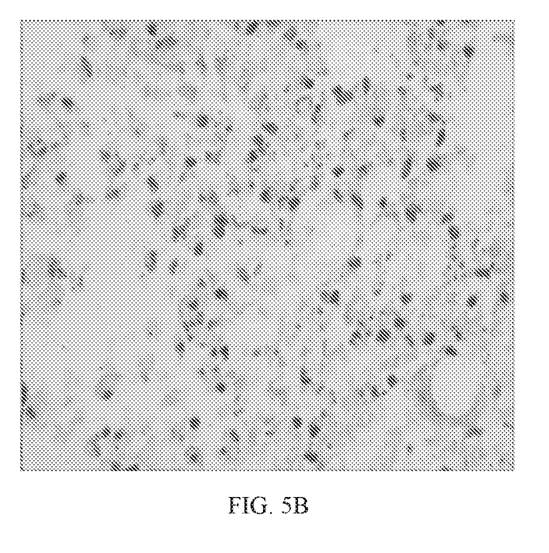
FIG. 5B shows an immunohistochemical staining result for COL2A1 treated with 1 µM BM23 peptide.

As shown in FIGS. 5A and 5B, the immunohistochemical staining for COL2A1 was more obvious in the 1 μM BM23 peptide treatment group than in the PBS treatment group, indicating that the expression level of COL2A1 protein was significantly increased.

Based on the above results, the expression levels of COL2A1 and ACAN which are used as cartilage marker genes are increased, indicating that BM23 peptide promotes the differentiation of mesenchymal stem cells into chondrocytes.

Embodiment 4

Isolation and Culture of Chondrocytes

The articular cartilage of New Zealand white rabbit aged 2 months old was cut under sterile conditions, and cut into a size of 1 mm. The articular cartilage was digested at 37° C. according to the following procedure:
(1) digested with 2 mg/ml hyaluronidase for 45 minutes;
(2) digested with 2 mg/ml trypsin for 45 minutes; and
(3) digested with 4 mg/ml type II collagenase for 3 hours, washed, and then centrifuged (1500 r/min) for 5 minutes; and the precipitate was cultured in a DMEM medium containing 15% fetal bovine serum.

Embodiment 5

Effect of BM23 Peptide on the Proliferation of Chondrocytes In Vitro

Identification of Chondrocytes:

A small amount of primary chondrocytes were smeared, immunodetected with type I collagen antibody SABC, and turned into brownish yellow, indicating that type I collagen was secreted, and thus proving that the sample was chondrocytes.

Detection of the Proliferation of Chondrocytes by MTS Assay

Chondrocytes were inoculated in a 96-well plate at $2 \times 10^4$ cells/well, and different concentrations of BM23 peptides (0.1 μM, 0.3 μM, and 1 μM) were added; PBS was set as a negative control group, and IGF-1 (1 μM) was set as a positive control group.

The 96-well plate was placed in a 5% $CO_2$ saturated water-vapor carbon dioxide incubator for a culture at 37° C. for 5 days.

20 μl of MTS mixture was added to each well, and the culture was continued for 3-4 hours for coloration.

Before testing, the culture plate was shaken for 10 seconds to uniformly mix colors. The optical density (OD) of each well was measured at a wavelength of 570 nm on an enzyme-linked immunometric meter.

Immunohistochemical Detection of COL2A1

Chondrocytes were inoculated at $3.5 \times 10^5$ cells/ml in a 6-well culture plate with coverslips, and different concentrations of BM23 peptides were added; PBS was set as a negative control group, and IGF-1 was set as a positive control group.

The 6-well culture plate was placed in a 5% $CO_2$ saturated water-vapor carbon dioxide incubator for a culture at 37° C. for 5 days.

Immunohistochemical staining was performed as in Embodiment 3.

Results

Promoting Effect of BM23 Peptide on the Proliferation of Chondrocytes

Figure 6:
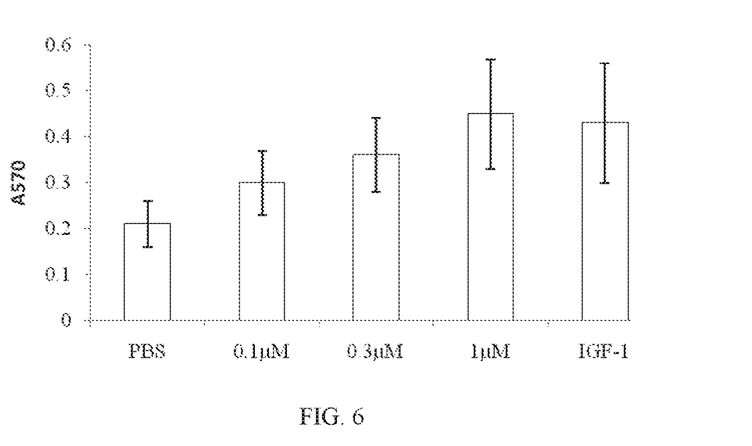
FIG. 6 shows an effect of a BM23 peptide on a proliferation of a rat chondrocyte; a cell proliferation was measured by a MTS method, PBS was used as a negative control, and IGF-1 was a positive control.

After 5 days of treatment with different concentrations of BM23 peptides, chondrocytes showed significant differences in proliferation. Compared with the PBS group, the proliferations of chondrocytes were significantly promoted in both BM23 peptide group and positive control group, as shown in FIG. 6.

Promoting Effect of BM23 Peptide on the Expression of COL2A1

Figure 7A:
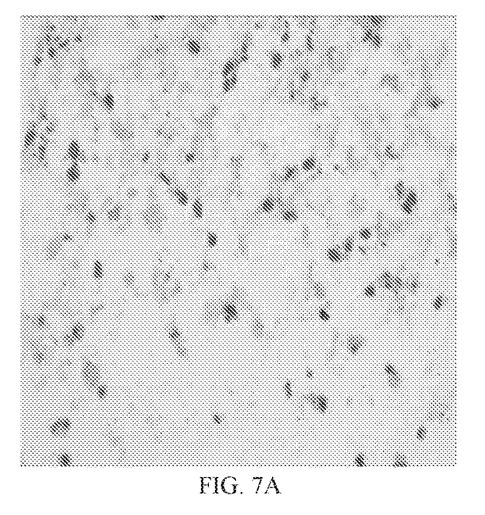
FIG. 7A shows an immunohistochemical result of COL2A1 of chondrocytes treated with a PBS.
Figure 7B:
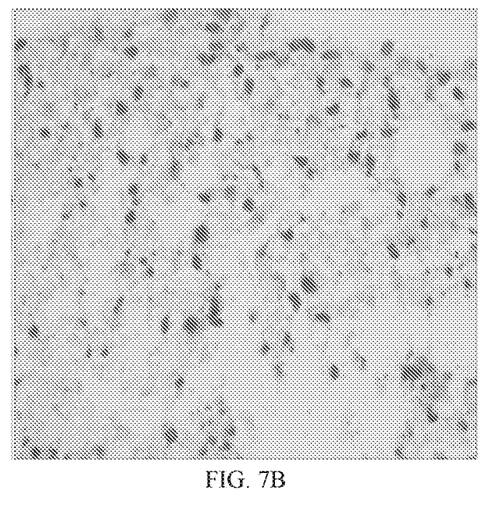
FIG. 7B shows an immunohistochemical staining result of COL2A1 treated with 1 µM BM23 peptide.

Compared with the PBS treatment group, the immunohistochemical staining of COL2A1 was more obvious in the 1 μM BM23 peptide treatment group, indicating the expression level of COL2A1 protein was significantly increased, as shown in FIGS. 7A and 7B.

Based on the above results, the BM23 peptide can promote the proliferation of chondrocytes in vitro.

Embodiment 6

Rabbit Cartilage Repair Model

Animals: New Zealand rabbits, 2 months old, half male and half female

Construction of models: New Zealand rabbits were anesthetized with 6% pentobarbital sodium (0.7 mL/kg) via marginal ear veins. After anesthesia, a longitudinal incision having a length of about 3 cm was made on the medial side of the knee joint of the left hind leg; the skin, subcutaneous tissue and joint capsule were cut successively to maintain the integrity of the patellar ligament; and the patella was turned outward to expose the femoral condyle. When the knee joint flexes 90°, an articular cartilage defect with a diameter of 4.2 mm and a depth of 3 mm was drilled in the femur and the middle of lateral intercondylar articular surfaces corresponding to the patella by using a drill bit with a diameter of 4.2 mm (according to visible bleeding on subchondral bone). The defect was washed with normal saline without any other treatment. After the humerus is reset, the muscle and skin incisions are sequentially sutured. After the patella is reset, the muscle and skin incisions are sequentially sutured. After the operation, immediately, the animals were intramuscularly injected with penicillin sodium once a day for 3 consecutive days to prevent infection.

Administration: the New Zealand rabbits with knee articular cartilage defects were divided into four groups: negative control group, low-dose group (1 mg/rabbit), medium-dose group (3 mg/rabbit) and high-dose group (10 mg/rabbit), 12 rabbits in each group, half male and half female in each group. On the $6^{th}$ day after constructing the models, each group of rabbits was administered intra-articularly. Namely, 1 mg/rabbit, 3 mg/rabbit and 10 mg/rabbit were administered to the test rabbits, respectively, and the administration volume was 0.2 ml.

Sacrifice and observation: at 90 days after the first administration, 6 rabbits (half male and half female) were selected from each group and sacrificed, and the repair situation of the knee articular cartilage in each rabbit was observed by dissection.

(1) General observation: during necropsy, the articular cavity was opened, the patella articular surface was exposed, and the repair of the filling edge of the defect, the flatness of the cartilage surface, the color of the new cartilage, etc., were observed.

Subsequently, scoring was performed according to the following criteria:

0 point: the articular surface is smooth and the color is normal;

1 point: the articular surface is rough, with small fissures and dark color;

2 points: the cartilage defect has reached the middle layer of cartilage;

3 points: the articular surface ulcer is formed, and the cartilage defect has reached the deep layer of cartilage; and 4 points: the cartilage is exfoliated, and subchondral bones are exposed.

(2) Histological pathological observation: observation was performed under light microscope, and scoring was performed according to the ICRS pathological scoring standard:

Grade 0: the cartilage surface is flat and the cartilage is intact;

Grade 1: the superficial fibers are formed in the cartilage surface and are uneven;

Grade 2: the cartilage surface is discontinuous, accompanied by cell proliferation; and metachromatic materials are increased or decreased in the II-III layers;

Grade 3: cartilage rhagadia has reached the III layer or erosion occurs;

Grade 4: the erosion of the cartilage is aggravated, and the articular cartilage is damaged;

Grade 5: the articular cartilage is exfoliated; and

Grade 6: the joint is deformed.

(3) HE staining

After the rabbits were sacrificed by anesthesia and exsanguination, the articular cartilage tissue was exfoliated and fixed with 10% neutral formalin, followed by dehydration, conventional paraffin embedding, sectioning, HE staining and mounting, and detection was performed by light microscopy.

Results

After 90 days of administration, the defect of knee joint in each rabbit was observed.

Negative Control Group:

The cartilage defect area was obviously sunk, and the surface was flat and complete; creeping growth was observed in the peripheral cartilages, but the color was dull; and the general observation score was 4.3 points.

Low-Dose Group:

The cartilage defect area was more obviously sunk, the surface was relatively flat; creeping growth was observed in the peripheral cartilages, but the color was dull; and the general observation score was 3.7 points.

Medium-Dose Group:

The cartilage defect area was not distinctly sunk as compared with the normal area, and the surface was flat and complete; the peripheral cartilages were covered, and the color was not different from that of normal cartilage; and the general observation score was 3.0 points.

High-Dose Group:

The cartilage defect area was not distinctly sunk as compared with the normal area, and the surface was flat and complete; the peripheral cartilages were covered, and the color was not different from that of normal cartilage; and the general observation score was 2.1 points.

Figure 8A:
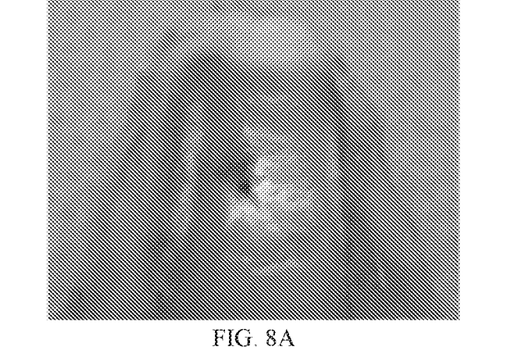
FIG. 8A shows a repair situation of cartilage 90 days after a first administration in a PBS treatment group.
Figure 8B:
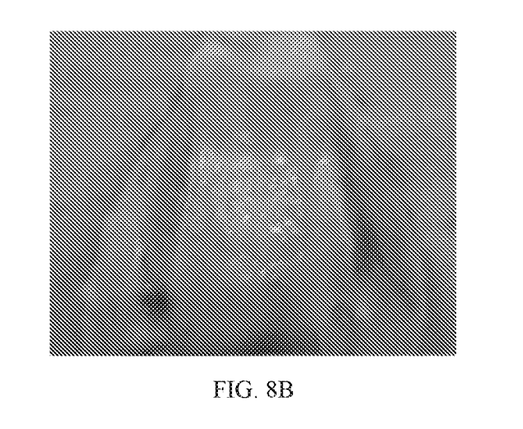
FIG. 8B shows a repair situation of cartilage 90 days after a first administration in a high-dose BM23 peptide treatment group.
Figure 9:
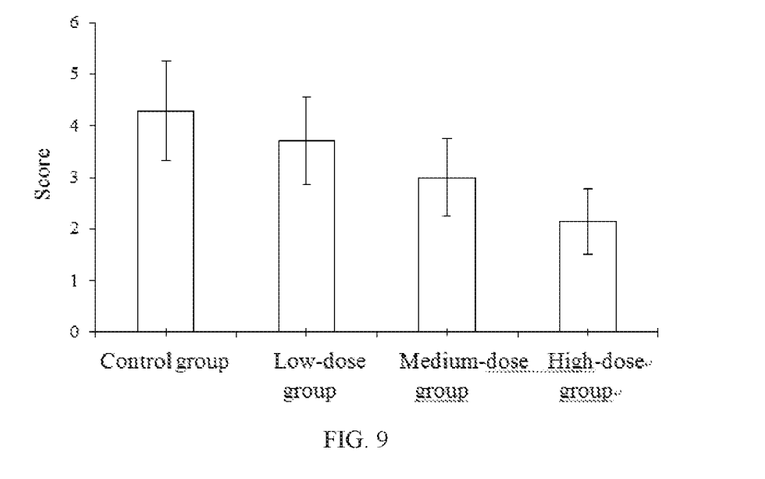
FIG. 9 shows general observation scores of a control group and a BM23 peptide group having different doses.

The general observation results are shown in FIG. 8, and the scores are shown in FIG. 9.

Histopathological Examination Results:

Negative Control Group:

For the selected six rabbits, the articular cavities were smooth and normal; the cartilage defect area was dominated by fibrous tissue hyperplasia with a small amount of chondrocytes; there were fissures at the junction and poor integration at both ends. The histopathological scores of articular cartilage of the selected six rabbits were 4.3 points.

Low-Dose Group:

For the selected six rabbits, the articular cavities were smooth and normal; the cartilage defect area was dominated by fibrous tissue hyperplasia with a small amount of chondrocytes; the surface layer of the defect was covered by cells, there were no fissures at the junction, and the two ends were well integrated. Among them, in one rabbit, creeping growth in the peripheral cartilages was observed, and a small amount of cartilage matrix was formed; and in one rabbit, the cartilage defect area was slightly sunk. The histopathological scores of articular cartilage of the selected six rabbits were 3.7 points.

Medium-Dose Group:

For the selected six rabbits, the articular cavities were smooth and normal; fibrous tissue hyperplasia occurred in the cartilage defect area, a large number of chondrocytes and cartilage matrix were formed; the surface layer was continuously covered by cells, the surface layer was irregular, there were no fissures at the junction, and the two ends were well integrated. The histopathological scores of articular cartilage of the selected six were 3.0 points.

High-Dose Group:

For the selected six rabbits, the articular cavities were smooth and normal; fibrous tissue hyperplasia occurred in the cartilage defect area, a large number of chondrocytes and cartilage matrix were formed; the surface layer was continuously covered by cells, there were no fissures at the junction, and the two ends were well integrated. The histopathological scores of articular cartilage of the selected six rabbits were 2.1 points.

Figure 10A:
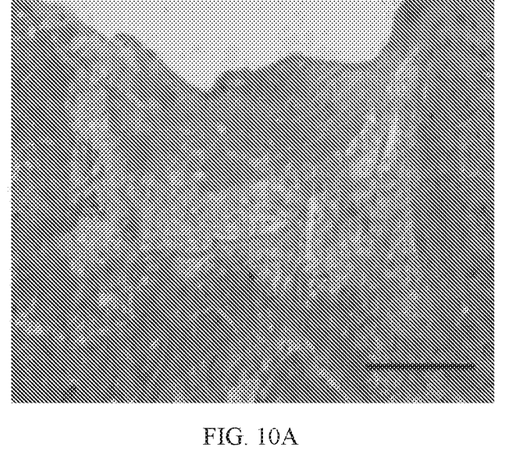
FIG. 10A shows a histopathological slice of cartilage 90 days after a first administration in a PBS treatment group.
Figure 10B:
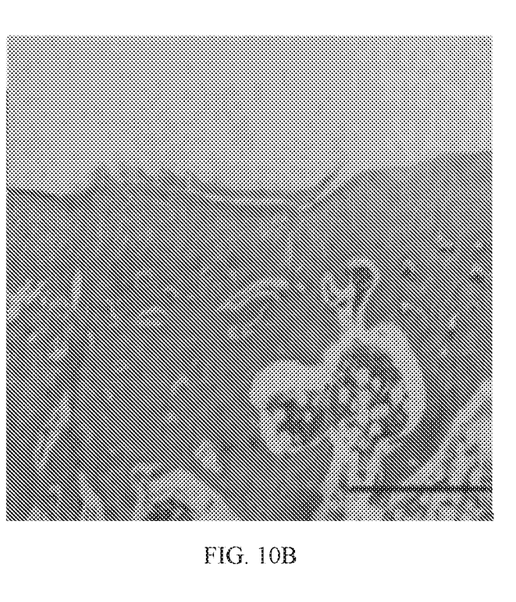
FIG. 10B shows a histopathological slice of cartilage 90 days after a first administration in a high-dose BM23 peptide treatment group.
Figure 11:
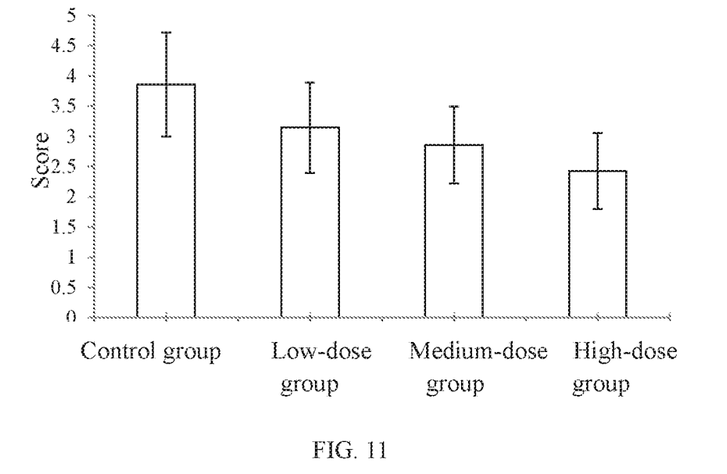
FIG. 11 shows histopathological scores of a control group and a BM23 peptide group having different doses.

The histopathological sections are shown in FIG. 10, and the scores are shown in FIG. 11.

The above results indicate that the BM23 peptide has a significant repair effect on cartilage damage in vivo, and this repair effect shows a dose-dependent relationship.

Embodiment 7

Comparison of Stabilities in Blood Plasma

Blood plasma preparation: 10 ml of anticoagulant whole blood were sampled from healthy volunteers, and centrifuged at 2000 rpm for 10 minutes; the pale yellow supernatant, i.e., plasma was taken.

BM23 peptide and BMP-2 (purchased from Beijing Yiqiao Shenzhou Biotechnology Co., Ltd.) were respectively incubated with human plasma at 37° C. at a final concentration of 50 µg/ml.

20 µl samples were taken at 10, 30, 60, 120, and 240 minutes, and the contents of BM23 peptide and BMP-2 in blood plasma were detected by HPLC, expressed as relative peak area (%).

Figure 12:
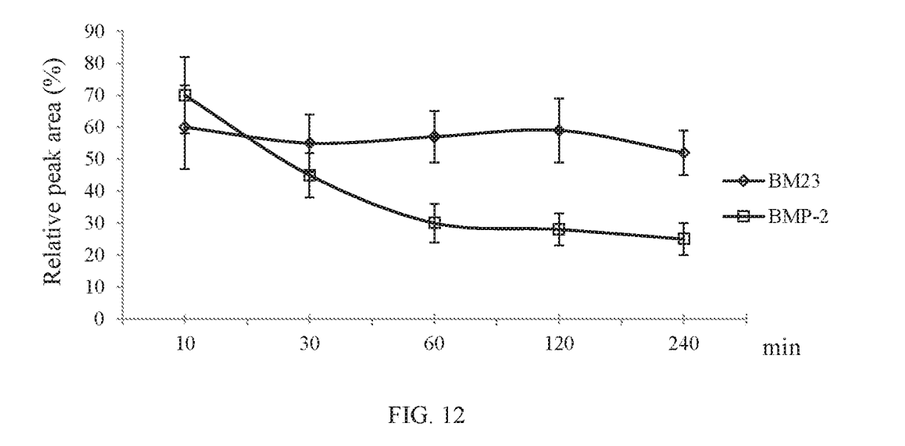
FIG. 12 shows a comparison result of stabilities of a BM23 peptide and a BMP-2 in blood plasma.

Results: after incubated in blood plasma for 4 hours, the concentration of BM23 peptide remained stable; while the concentration of BMP-2 decreased significantly after BMP-2 was incubated in blood plasma for 30 minutes (FIG. 12), indicating that the stability of BM23 peptide in blood plasma was better than that of BMP-2.

Embodiment 8

Comparison of In-Vivo Blood Plasma Elimination Half-Life

In order to confirm that the synthesized BM23 peptide has a relatively long half-life, the half-life of BM23 peptide and BMP-2 in rabbits were detected by LC/MSMS method.

LC/MSMS methodology was established, Finnigan TSQ Discovery Max LC/MS was equipped with Surveyor HPLC system. The detection limit was 1-1000 ng/ml, and the recovery rate was over 80%.

Six New Zealand rabbits were randomly divided into two groups (three rabbits in each group). The two groups were intravenously injected with 0.5 mg/kg of BM23 peptide and 0.5 mg/kg of BMP-2, respectively; 0.5 ml of blood samples were taken at 5, 10, 15, 30, 60, 120, 180, 300 minutes and placed in an anticoagulant tube, respectively; and centrifuged at 2000 rpm to remove the blood plasma, and then stored at −20° C. for measurement.

The blood concentration was measured by LC/MSMS method, 100 µl of blood plasma was taken, 500 µl of a mixed solvent containing IS 2000 ng/ml of acetonitrile and methanol solution at a ratio of 70:30 was added, shaken, and centrifuged at 12000 rpm for 10 minutes. 20 µl of supernatant was injected for LC/MSMS analysis. The main pharmacokinetic parameters were calculated by using 3P97 pharmacokinetic software.

Figure 13:
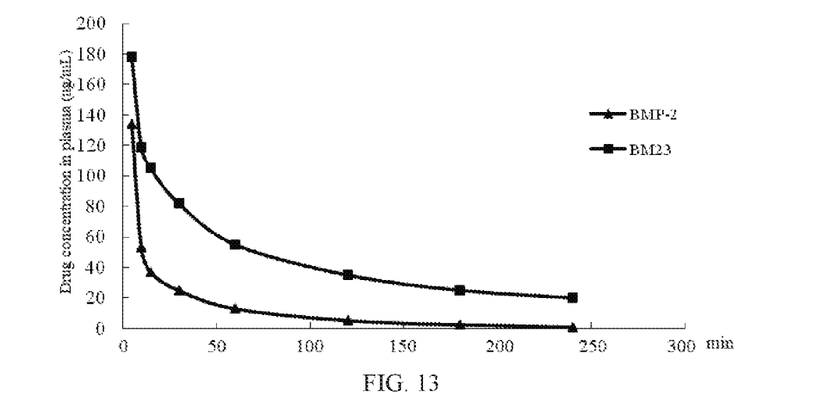
FIG. 13 shows a comparison result of blood plasma elimination half-life of a BM23 peptide and a BMP-2.

The results showed that the half-life of BM23 peptide was 123±38 minutes, the half-life of BMP-2 was 23±11 minutes, and the half-life of BM23 peptide was significantly longer than that of BMP-2 (FIG. 13). The longer half-life of the BM23 peptide is beneficial to the long-lasting effect of the drug and reduces the frequency of administration.

It can be concluded from the above embodiments that the BM23 peptide of the present invention can promote the differentiation of mesenchymal stem cells into chondrocytes, and stimulate the proliferation of chondrocytes. In vivo, BM23 peptide has a significant repair effect on cartilage damage, and this repair effect showed dose-dependent relationship. Moreover, the stability of BM23 peptide in blood plasma is better than that of BMP-2, and the in-vivo blood plasma elimination half-life of BM23 peptide is also significantly longer than that of BMP-2. Therefore, the BM23 peptide of the present invention exhibits superior stability to BMP-2, has a longer action time, and can be used for repairing cartilage and/or treating osteoarthritis.

What is claimed is:

1. A peptide, comprising 23 amino acids, wherein a sequence of the peptide is as shown in SEQ ID NO: 1, wherein the 1$^{st}$ amino acid of the sequence is D-glutamine, the 7$^{th}$ amino acid of the sequence is homoarginine, and the 23$^{rd}$ amino acid of the sequence is amidated leucine.

2. The peptide according to claim 1, wherein the peptide is used to repair cartilage and/or treat osteoarthritis.

3. The peptide according to claim 1, wherein a carboxyl terminus of the peptide is subjected to an amidation.

4. The peptide according to claim 1, wherein the peptide for a treatment of a cartilage damage and/or osteoarthritis is 1-10 mg.

5. The peptide according to claim 1, wherein the peptide is modified to form a chimeric molecule; and the chimeric molecule comprises a fusion protein formed by a fusion of the peptide with an immunoglobulin constant region (Fc) or a human serum albumin (HSA).

6. The peptide according to claim 1, wherein the peptide is used to treat osteoarthritis in combination with osteoarthritis drugs; and the osteoarthritis drugs comprises hyaluronic acid, or non-steroidal anti-inflammatory drugs.

7. A pharmaceutically acceptable salt of a peptide, comprising: hydrochlorides, phosphates or acetates, wherein the peptide comprises 23 amino acids, a sequence of the peptide is as shown in SEQ ID NO: 1, the 1$^{st}$ amino acid of the sequence is D-glutamine, the 7$^{th}$ amino acid of the sequence is homoarginine, and the 23$^{rd}$ amino acid of the sequence is amidated leucine.

8. A drug, comprising a peptide at a therapeutically effective dose and a pharmaceutically acceptable carrier, wherein the peptide comprises 23 amino acids, a sequence of the peptide is as shown in SEQ ID NO: 1, the 1$^{st}$ amino acid of the sequence is D-glutamine, the 7$^{th}$ amino acid of the sequence is homoarginine, and the 23$^{rd}$ amino acid of the sequence is amidated leucine.

9. The drug according to claim 8, wherein the pharmaceutically acceptable carrier is a saline solution, and the drug is injectable.

10. The drug according to claim 8, wherein the pharmaceutically acceptable carrier is a hyaluronic acid gel; and the drug is injectable.

11. The drug according to claim 8, wherein the drug is administrated by a knee articular cavity injection or a subcutaneous injection.

12. The peptide according to claim 2, wherein a carboxyl terminus of the peptide is subjected to an amidation.

13. The peptide according to claim 2, wherein the peptide for a treatment of a cartilage damage and/or osteoarthritis is 1-10 mg.

14. The peptide according to claim 3, wherein of the peptide for a treatment of a cartilage damage and/or osteoarthritis is 1-10 mg.

15. The peptide according to claim 2, wherein the peptide is modified to form a chimeric molecule; and the chimeric molecule comprises a fusion protein formed by a fusion of the peptide with an immunoglobulin constant region (Fc) or a human serum albumin (HSA).

16. The peptide according to claim 3, wherein the peptide is modified to form a chimeric molecule; and the chimeric molecule comprises a fusion protein formed by a fusion of the peptide with an immunoglobulin constant region (Fc) or a human serum albumin (HSA).

17. The peptide according to claim 4, wherein the peptide is modified to form a chimeric molecule; and the chimeric molecule comprises a fusion protein formed by a fusion of the peptide with an immunoglobulin constant region (Fc) or a human serum albumin (HSA).

18. The peptide according to claim 2, wherein the peptide is used to treat osteoarthritis in combination with osteoarthritis drugs; and the osteoarthritis drugs comprises hyaluronic acid, or non-steroidal anti-inflammatory drugs.

19. The peptide according to claim 3, wherein the peptide is used to treat osteoarthritis in combination with osteoarthritis drugs; and the osteoarthritis drugs comprises hyaluronic acid, or non-steroidal anti-inflammatory drugs.

\* \* \* \* \*

SEQUENCE LISTING

```
<160> NUMBER OF SEQ ID NOS: 5

<210> SEQ ID NO 1
<211> LENGTH: 23
<212> TYPE: PRT
<213> ORGANISM: Artificial Sequence
<220> FEATURE:
<223> OTHER INFORMATION: The sequence is a synthesized and modified
      amino acid sequence
<220> FEATURE:
<221> NAME/KEY: MISC_FEATURE
<222> LOCATION: (1)..(1)
<223> OTHER INFORMATION: the Gln is D-glutamine
<220> FEATURE:
<221> NAME/KEY: MISC_FEATURE
<222> LOCATION: (7)..(7)
<223> OTHER INFORMATION: the Xaa is homoarginine, Har
<220> FEATURE:
<221> NAME/KEY: AMIDATION
<222> LOCATION: (23)..(23)
<223> OTHER INFORMATION: the Leu is amidated leucine; generally at the
      C-terminal of a mature active peptide

<400> SEQUENCE: 1

Gln Leu Lys His Arg Asn Xaa His Arg Ile Lys Thr Gly Ser Thr Asn
1               5                   10                  15

His Gly Leu Val Gln Ser Leu
            20

<210> SEQ ID NO 2
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 2
gcggagacta ctggattgat                                               20

<210> SEQ ID NO 3
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 3
cgttcatggt ctctccaaac                                               20

<210> SEQ ID NO 4
<211> LENGTH: 20
<212> TYPE: DNA
<213> ORGANISM: Artificial Sequence
<220> FEATURE:
<223> OTHER INFORMATION: The sequence is synthesized
```

```
<400> SEQUENCE: 4
gagttcccag atctgcatgg                                          20

<210> SEQ ID NO 5
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 5
tggtgctgac ggtaacattc                                          20
```